United States Patent
Murray et al.

(10) Patent No.: US 6,544,520 B1
(45) Date of Patent: Apr. 8, 2003

(54) HEPATITIS B VIRUS INHIBITORS

(75) Inventors: Kenneth Murray, Edinburgh (GB); Michael Richard Dyson, Edinburgh (GB)

(73) Assignee: Biogen, Inc., Cambridge, MA (US)

(*) Notice: Subject to any disclaimer, the term of this patent is extended or adjusted under 35 U.S.C. 154(b) by 0 days.

(21) Appl. No.: 09/302,087

(22) Filed: Apr. 29, 1999

Related U.S. Application Data

(63) Continuation of application No. PCT/US97/19965, filed on Oct. 31, 1997.
(60) Provisional application No. 60/030,534, filed on Oct. 31, 1996.

(51) Int. Cl.$^7$ .................. A61K 39/00; A61K 38/08; A61K 38/10; C12Q 1/70; C07K 7/00
(52) U.S. Cl. .................. 424/185.1; 514/14; 514/15; 514/16; 435/5; 530/327; 530/328
(58) Field of Search .................. 435/5; 424/185.1, 424/189.1; 530/327, 328; 514/12, 14, 15, 16

(56) References Cited

U.S. PATENT DOCUMENTS

| | | | |
|---|---|---|---|
| 5,204,096 A | 4/1993 | Neurath et al. | 424/89 |
| 5,204,446 A | 4/1993 | Kumazawa et al. | 530/325 |
| 5,378,814 A | 1/1995 | Houghton et al. | 530/350 |
| 5,436,126 A | 7/1995 | Wang | 435/5 |
| 5,512,648 A | 4/1996 | Sparrow et al. | 526/307 |
| 5,531,990 A | 7/1996 | Thanavala et al. | 424/131.1 |
| 5,547,669 A | 8/1996 | Rogers et al. | 424/185.1 |
| 5,556,744 A | 9/1996 | Weiner et al. | 435/5 |

FOREIGN PATENT DOCUMENTS

| | | |
|---|---|---|
| WO | WO 96/39502 | 12/1996 |

OTHER PUBLICATIONS

D. Ganem et al., "The Molecular Biology of the Hepatitis B. Viruses," *Ann. Rev. Biochem.,* 56, pp. 651–693, (1987).

K. Murray et al., "Hepatitis B Virus Antigens made in Microbial Cells Immunise against Viral Infection," *EMBO Journal,* 30, pp. 645–650 (1984).

A.R. Neurath et al., "Specificity of Antibodies Elicited by a Synthetic Peptide having a Sequence in Common with a Fragment of a Virus Protein, the Hepatitis B Surface Antigen," *Proc. Natl. Acad. Sci. USA,* 79, pp. 7871–7875.

H.L. Niman et al., "Generation of Protein–Reactive Antibodies by Short Peptides is an Event of High Frequency: Implications for the Structural Basis of Immune Recognition," *Proc. Natl. Acad. Sci. USA,* 80, pp. 4949–4953, (1983).

H. Takahashi et al., "Acute Hepatitis in Rats Expressing Human Hepatitis B Virus Transgenes", *Proc. Natl. Acad. Sci. USA,* 92, pp. 1470–1474 (1995).

K. Ueda et al., "Three Envelope Proteins of Hepatitis B Virus: Large S, Middle S and Major S Proteins Needed for the Formation of Dane Particles", *J. Virol.,* 65, pp. 3521–3529 (1991).

Dyson, et al. Selection of peptide inhibitors of interactions involved in complex protein assemblies: Association of the core and surface antigens of Hepatitis B virus. Proc. Natl. Acad. Sci. Mar., 1995. vol. 92, pp. 2194–2198.*

Murray et al. Journal of Medical Virology. 1987; 23: 101–107.*

Bottcher et al. The EMBO Journal. 1998; 17 (23): 6839–6845.*

Cruse et al. Illustrated Dictionary of Immunology. 1995. Boca Raton: CRC Press.*

V. Bruss et al., "The role of envelope proteins in hepatitis B virus assembly," *Proc. Natl. Acad. Sci.,* 88, pp. 1059–1063 (1991).

N.C. Collier et al., "Inhibition of Influenza Virus Formation by a Peptide That Corresponds to Sequences in the Cytoplasmic Domain of the Hemagglutinin," *Virology,* 183, pp. 769–772 (1991).

M.R. Dyson et al., "Direct measurement via phage titre of the dissociation constants in solution of fusion phage–substrate complexes," *Nucleic Acids Res.,* 23, pp. 1531–1535 (1995).

D.A. Fallows et al., "Hepadnaviruses: Current Models of RNA Encapsidation and Reverse Transcription," *Advances in Virus Research,* 46, pp. 165–194 (1996).

V. Germaschewski et al., "Screening a Monoclonal Antibody With a Fusion–Phage Display Library Shows a Discontinuity in a Linear Epitope Within PreS1 of Hepatitis B Virus," *J. Med. Virol.,* 45, pp. 300–305 (1995).

S.S. Hong et al., "Protein ligands of the human adenovirus type 2 outer capsid identified by biopanning of a phage–displayed peptide library on separate domains of wild–type and mutant penton capsomers," *EMBO J.,* 14, pp. 4714–4727 (1995).

B.B. Knowles et al., "Human Hepatocellular Carcinoma Cell Lines Secrete the Major Plasma Proteins and Hepatitis B Surface Antigen," *Science,* 209, pp. 497–499 (1980).

(List continued on next page.)

*Primary Examiner*—James Housel
*Assistant Examiner*—Shanon Foley
(74) *Attorney, Agent, or Firm*—Fish & Neave; James F. Haley, Jr.; Margaret A. Pierri

(57) ABSTRACT

Peptides and other molecules which inhibit the assembly of the hepatitis B virus, methods of treatment, and pharmaceutical compositions comprising them.

25 Claims, No Drawings

OTHER PUBLICATIONS

M. Nassal et al., "Topological Analysis of the Hepatitis B Virus Core Particle by Cysteine–Cysteine Cross–linking," *J. Mol. Biol.,* 225, pp. 1013–1025 (1992).

P.C.N. Rensen et al., "Selective liver targeting of antivirals by recombinant chylomicrons—a new therapeutic approach to hepatitis B," *Nat. Med.,* 1, pp. 221–225 (1995).

J.K. Scott et al., "Searching for Peptide Ligands with an Epitope Library," *Science,* 249, pp. 386–390 (1990).

L. Weiss et al., "The HBV–Producing Cell Line HepG2–A45: A New in vitro System for Studying the Regulation of HBV Replication and for Screening Anti–Hepatitis B Virus Drugs," *Virology,* 216, pp. 214–218 (1996).

J. Zheng et al., "The Structure of Hepadnaviral Core Antigens," *J. Biol. Chem.,* 267, pp. 9422–9429 (1992).

\* cited by examiner

SEQUENCE LISTING

<160> NUMBER OF SEQ ID NOS: 38

<210> SEQ ID NO 1
<211> LENGTH: 12
<212> TYPE: PRT
<213> ORGANISM: Artificial Sequence
<220> FEATURE:
<223> OTHER INFORMATION: HBV Core Antigen Binding Peptide

<400> SEQUENCE: 1

Ala Asp Gly Ala Leu Leu Gly Arg Met Lys Gly Ala
1               5                   10

<210> SEQ ID NO 2
<211> LENGTH: 12
<212> TYPE: PRT
<213> ORGANISM: Artificial Sequence
<220> FEATURE:
<223> OTHER INFORMATION: HBV Core Antigen Binding Peptide

<400> SEQUENCE: 2

Ala Asp Gly Ala Leu Leu Gly Arg Met Lys Pro Ala
1               5                   10

<210> SEQ ID NO 3
<211> LENGTH: 12
<212> TYPE: PRT
<213> ORGANISM: Artificial Sequence
<220> FEATURE:
<223> OTHER INFORMATION: HBV Core Antigen Binding Peptide

<400> SEQUENCE: 3

Ala Asp Gly Ser Leu Leu Gly Arg Met Lys Pro Ala
1               5                   10

<210> SEQ ID NO 4
<211> LENGTH: 12
<212> TYPE: PRT
<213> ORGANISM: Artificial Sequence
<220> FEATURE:
<223> OTHER INFORMATION: HBV Core Antigen Binding Peptide

<400> SEQUENCE: 4

Ala Asp Gly Ala Leu Leu Gly Arg Met Lys Arg Ala
1               5                   10

<210> SEQ ID NO 5
<211> LENGTH: 12
<212> TYPE: PRT
<213> ORGANISM: Artificial Sequence
<220> FEATURE:
<223> OTHER INFORMATION: HBV Core Antigen Binding Peptide

<400> SEQUENCE: 5

Ala Asp Gly Thr Leu Leu Gly Arg Met Lys Leu Ala
1               5                   10

<210> SEQ ID NO 6
<211> LENGTH: 12
<212> TYPE: PRT
<213> ORGANISM: Artificial Sequence
<220> FEATURE:
<223> OTHER INFORMATION: HBV Core Antigen Binding Peptide

<400> SEQUENCE: 6

```
Ala Asp Gly Ser Leu Leu Gly Arg Met Lys Gly Ala
1               5                   10
```

<210> SEQ ID NO 7
<211> LENGTH: 12
<212> TYPE: PRT
<213> ORGANISM: Artificial Sequence
<220> FEATURE:
<223> OTHER INFORMATION: HBV Core Antigen Binding Peptide

<400> SEQUENCE: 7

```
Ala Asp Arg Ser Leu Leu Gly Arg Met Lys Gly Ala
1               5                   10
```

<210> SEQ ID NO 8
<211> LENGTH: 15
<212> TYPE: PRT
<213> ORGANISM: Artificial Sequence
<220> FEATURE:
<223> OTHER INFORMATION: HBV Core Antigen Binding Peptide

<400> SEQUENCE: 8

```
Ala Asp Gly Ser Arg Ser Ser Leu Leu Gly Arg Met Lys Gly Ala
1               5                   10                  15
```

<210> SEQ ID NO 9
<211> LENGTH: 15
<212> TYPE: PRT
<213> ORGANISM: Artificial Sequence
<220> FEATURE:
<223> OTHER INFORMATION: HBV Core Antigen Binding Peptide

<400> SEQUENCE: 9

```
Ala Asp Gly Ala His Ser Ser Leu Leu Gly Arg Met Lys Gly Ala
1               5                   10                  15
```

<210> SEQ ID NO 10
<211> LENGTH: 15
<212> TYPE: PRT
<213> ORGANISM: Artificial Sequence
<220> FEATURE:
<223> OTHER INFORMATION: HBV Core Antigen Binding Peptide

<400> SEQUENCE: 10

```
Ala Asp Gly His Arg Ser Ser Leu Leu Gly Arg Met Lys Gly Ala
1               5                   10                  15
```

<210> SEQ ID NO 11
<211> LENGTH: 15
<212> TYPE: PRT
<213> ORGANISM: Artificial Sequence
<220> FEATURE:
<223> OTHER INFORMATION: HBV Core Antigen Binding Peptide

<400> SEQUENCE: 11

```
Ala Asp Gly Pro Arg Ser Ser Leu Leu Gly Arg Met Lys Gly Ala
1               5                   10                  15
```

<210> SEQ ID NO 12
<211> LENGTH: 15
<212> TYPE: PRT
<213> ORGANISM: Artificial Sequence
<220> FEATURE:
<223> OTHER INFORMATION: HBV Core Antigen Binding Peptide

<400> SEQUENCE: 12

```
Ala Asp Gly Ala His Arg Ser Leu Leu Gly Arg Met Lys Gly Ala
```

```
                1               5              10              15
```

<210> SEQ ID NO 13
<211> LENGTH: 15
<212> TYPE: PRT
<213> ORGANISM: Artificial Sequence
<220> FEATURE:
<223> OTHER INFORMATION: HBV Core Antigen Binding Peptide

<400> SEQUENCE: 13

```
Ala Asp Gly Tyr Gln Arg Ser Leu Leu Gly Arg Met Lys Gly Ala
1               5                   10                  15
```

<210> SEQ ID NO 14
<211> LENGTH: 15
<212> TYPE: PRT
<213> ORGANISM: Artificial Sequence
<220> FEATURE:
<223> OTHER INFORMATION: HBV Core Antigen Binding Peptide

<400> SEQUENCE: 14

```
Ala Asp Gly Thr Gln Arg Ser Leu Leu Gly Arg Met Lys Gly Ala
1               5                   10                  15
```

<210> SEQ ID NO 15
<211> LENGTH: 15
<212> TYPE: PRT
<213> ORGANISM: Artificial Sequence
<220> FEATURE:
<223> OTHER INFORMATION: HBV Core Antigen Binding Peptide

<400> SEQUENCE: 15

```
Ala Asp Gly Met His Arg Ser Leu Leu Gly Arg Met Lys Gly Ala
1               5                   10                  15
```

<210> SEQ ID NO 16
<211> LENGTH: 8
<212> TYPE: PRT
<213> ORGANISM: Artificial Sequence
<220> FEATURE:
<223> OTHER INFORMATION: HBV Core Antigen Binding Peptide

<400> SEQUENCE: 16

```
Ala Leu Leu Gly Arg Met Lys Gly
1               5
```

<210> SEQ ID NO 17
<211> LENGTH: 7
<212> TYPE: PRT
<213> ORGANISM: Artificial Sequence
<220> FEATURE:
<223> OTHER INFORMATION: HBV Core Antigen Binding Peptide

<400> SEQUENCE: 17

```
Leu Leu Gly Arg Met Lys Gly
1               5
```

<210> SEQ ID NO 18
<211> LENGTH: 6
<212> TYPE: PRT
<213> ORGANISM: Artificial Sequence
<220> FEATURE:
<223> OTHER INFORMATION: HBV Core Antigen Binding Peptide

<400> SEQUENCE: 18

```
Leu Gly Arg Met Lys Gly
1               5
```

```
<210> SEQ ID NO 19
<211> LENGTH: 5
<212> TYPE: PRT
<213> ORGANISM: Artificial Sequence
<220> FEATURE:
<223> OTHER INFORMATION: HBV Core Antigen Binding Peptide

<400> SEQUENCE: 19

Gly Arg Met Lys Gly
1               5

<210> SEQ ID NO 20
<211> LENGTH: 5
<212> TYPE: PRT
<213> ORGANISM: Artificial Sequence
<220> FEATURE:
<223> OTHER INFORMATION: HBV Core Antigen Binding Peptide

<400> SEQUENCE: 20

Leu Leu Gly Arg Met
1               5

<210> SEQ ID NO 21
<211> LENGTH: 8
<212> TYPE: PRT
<213> ORGANISM: Artificial Sequence
<220> FEATURE:
<223> OTHER INFORMATION: HBV Core Antigen Binding Peptide

<400> SEQUENCE: 21

Cys Leu Leu Gly Arg Met Lys Cys
1               5

<210> SEQ ID NO 22
<211> LENGTH: 8
<212> TYPE: PRT
<213> ORGANISM: Artificial Sequence
<220> FEATURE:
<223> OTHER INFORMATION: HBV Core Antigen Binding Peptide

<400> SEQUENCE: 22

Ala Leu Leu Pro Arg Met Lys Gly
1               5

<210> SEQ ID NO 23
<211> LENGTH: 8
<212> TYPE: PRT
<213> ORGANISM: Artificial Sequence
<220> FEATURE:
<223> OTHER INFORMATION: HBV Core Antigen Binding Peptide

<400> SEQUENCE: 23

Ser Leu Leu Gly Arg Met Lys Gly
1               5

<210> SEQ ID NO 24
<211> LENGTH: 7
<212> TYPE: PRT
<213> ORGANISM: Artificial Sequence
<220> FEATURE:
<223> OTHER INFORMATION: HBV Core Antigen Binding Peptide

<400> SEQUENCE: 24

Ser Leu Leu Gly Arg Met Lys
1               5
```

<210> SEQ ID NO 25
<211> LENGTH: 9
<212> TYPE: PRT
<213> ORGANISM: Artificial Sequence
<220> FEATURE:
<223> OTHER INFORMATION: HBV Core Antigen Binding Peptide

<400> SEQUENCE: 25

Ser Leu Leu Gly Arg Met Lys Gly Ala
1               5

<210> SEQ ID NO 26
<211> LENGTH: 10
<212> TYPE: PRT
<213> ORGANISM: Artificial Sequence
<220> FEATURE:
<223> OTHER INFORMATION: HBV Core Antigen Binding Peptide

<400> SEQUENCE: 26

Gly Ser Leu Leu Gly Arg Met Lys Gly Ala
1               5                   10

<210> SEQ ID NO 27
<211> LENGTH: 12
<212> TYPE: PRT
<213> ORGANISM: Artificial Sequence
<220> FEATURE:
<223> OTHER INFORMATION: HBV Core Antigen Binding Peptide

<400> SEQUENCE: 27

Asp Gly Ser Leu Leu Gly Arg Met Lys Gly Ala Ala
1               5                   10

<210> SEQ ID NO 28
<211> LENGTH: 14
<212> TYPE: PRT
<213> ORGANISM: Artificial Sequence
<220> FEATURE:
<223> OTHER INFORMATION: HBV Core Antigen Binding Peptide

<400> SEQUENCE: 28

Ala Asp Gly Ser Leu Leu Gly Arg Met Lys Gly Ala Ala Gly
1               5                   10

<210> SEQ ID NO 29
<211> LENGTH: 8
<212> TYPE: PRT
<213> ORGANISM: Artificial Sequence
<220> FEATURE:
<223> OTHER INFORMATION: HBV Core Antigen Binding Peptide
<221> NAME/KEY: MOD_RES
<222> LOCATION: (1)..(1)
<223> OTHER INFORMATION: ACETYLATION

<400> SEQUENCE: 29

Ser Leu Leu Gly Arg Met Lys Gly
1               5

<210> SEQ ID NO 30
<211> LENGTH: 10
<212> TYPE: PRT
<213> ORGANISM: Artificial Sequence
<220> FEATURE:
<223> OTHER INFORMATION: HBV Core Antigen Binding Peptide
<221> NAME/KEY: MISC_FEATURE
<222> LOCATION: (9)..(9)
<223> OTHER INFORMATION: bAla

```
<400> SEQUENCE: 30

Ser Leu Leu Gly Arg Met Lys Gly Xaa Cys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: HBV Core Antigen Binding Peptide

<400> SEQUENCE: 31

Arg Ser Leu Leu Gly Arg Met Lys Gly Ala
1               5                   10

<210> SEQ ID NO 32
<211> LENGTH: 11
<212> TYPE: PRT
<213> ORGANISM: Artificial Sequence
<220> FEATURE:
<223> OTHER INFORMATION: HBV Core Antigen Binding Peptide

<400> SEQUENCE: 32

His Arg Ser Leu Leu Gly Arg Met Lys Gly Ala
1               5                   10

<210> SEQ ID NO 33
<211> LENGTH: 12
<212> TYPE: PRT
<213> ORGANISM: Artificial Sequence
<220> FEATURE:
<223> OTHER INFORMATION: HBV Core Antigen Binding Peptide

<400> SEQUENCE: 33

Met His Arg Ser Leu Leu Gly Arg Met Lys Gly Ala
1               5                   10

<210> SEQ ID NO 34
<211> LENGTH: 12
<212> TYPE: PRT
<213> ORGANISM: Artificial Sequence
<220> FEATURE:
<223> OTHER INFORMATION: HBV Core Antigen Binding Peptide
<221> NAME/KEY: MISC_FEATURE
<222> LOCATION: (11)..(11)
<223> OTHER INFORMATION: bAla

<400> SEQUENCE: 34

Arg Ser Leu Leu Gly Arg Met Lys Gly Ala Xaa Cys
1               5                   10

<210> SEQ ID NO 35
<211> LENGTH: 16
<212> TYPE: PRT
<213> ORGANISM: Artificial Sequence
<220> FEATURE:
<223> OTHER INFORMATION: HBV Core Antigen Binding Peptide
<221> NAME/KEY: MISC_FEATURE
<222> LOCATION: (14)..(14)
<223> OTHER INFORMATION: bAla

<400> SEQUENCE: 35

Met His Arg Ser Leu Leu Gly Arg Met Lys Gly Ala Gly Xaa Gly Cys
1               5                   10                  15

<210> SEQ ID NO 36
<211> LENGTH: 6
```

```
<212> TYPE: PRT
<213> ORGANISM: Artificial Sequence
<220> FEATURE:
<223> OTHER INFORMATION: HBV Core Antigen Binding Peptide

<400> SEQUENCE: 36

Leu Leu Gly Arg Met Lys
1               5

<210> SEQ ID NO 37
<211> LENGTH: 8
<212> TYPE: PRT
<213> ORGANISM: Artificial Sequence
<220> FEATURE:
<223> OTHER INFORMATION: HBV Core Antigen Binding Peptide

<400> SEQUENCE: 37

Ala Leu Leu Thr Arg Ile Leu Gly
1               5

<210> SEQ ID NO 38
<211> LENGTH: 6
<212> TYPE: PRT
<213> ORGANISM: Artificial Sequence
<220> FEATURE:
<223> OTHER INFORMATION: HBV Core Antigen Binding Peptide

<400> SEQUENCE: 38

Leu Asp Pro Ala Phe Arg
1               5
```

HEPATITIS B VIRUS INHIBITORS

CROSS-REFERENCE TO RELATED APPLICATIONS

This application is a continuation of PCT International application PCT/US97/19965, filed Oct. 31, 1997, which claims priority from U.S. application Ser. No. 60/030,534, filed Oct. 31, 1996.

TECHNICAL FIELD OF THE INVENTION

Peptides and other molecules which inhibit the assembly of the hepatitis B virus, methods of treatment, and pharmaceutical compositions comprising them.

BACKGROUND OF THE INVENTION

The present invention relates to peptide compositions specific for the diagnosis, treatment or prevention of hepatitis B virus infection.

Hepatitis B virus ("HBV") infects human at a very high rate. It is estimated that at least about 300 million people are chronic carriers of HBV. Despite extensive research, additional safe and effective therapies remain to be identified.

HBV infections thus continue to represent a major public health problem worldwide. Infection with the virus results in a gamut of clinical symptoms ranging from minor flu-like symptoms to death. Available vaccines produced from the serum of HBV carriers do not provide the appropriate means to control and eradicate the disease worldwide because of limited resources and production costs involved. Vaccines produced based upon recombinant DNA technology overcome some of these disadvantages, however, there is still a need for additional means to control and eradicate the HBV virus.

The biology, structure and immunochemistry of HBV and the genetic organization of its DNA genome are known. Ganem, D., Varmus, H. E., Ann. Rev. Biochem. 56: 651–693 (1987). The virus is transmitted by three general mechanisms: (1) by inoculation with infected blood or body fluids, (2) by close family or sexual contact, or (3) by infection during pregnancy, where the mother transmits the virus to her child. HBV consists of a nucleocapsid, a small 3.2-kb DNA genome, and the viral polymerase enclosed by the core antigen of the virus, surrounded in turn by the HBV surface antigen (HBsAg). The viral envelope contains three different, but related HBsAg polypeptides, which overlap extensively from their carboxyl termini and arise from variable use of initiation triplets at different points within a continuous open reading frame. The long polypeptide (L polypeptide) is the product of the entire reading frame and comprises the pre-S 1 domain of 108 amino acids (or 119, depending on virus subtype) at its amino terminus, followed by the pre-S2 domain of 55 amino acids, and the short polypeptide (S polypeptide) region of 226 amino acids. The medium-length polypeptide (M polypeptide) has the pre-S2 domain at its amino terminus followed by the S region, whereas the S polypeptide, which is the most abundant form, consists of only the S region. The pre-S regions are believed to play a role in both viral assembly and attachment to the host cell. The S form is more abundant than the M and L forms of HBsAg in the virus, and occurs in both glycosylated and nonglycosylated forms. In addition to its presence in the viral envelope, HBsAg is found in large quantities in the serum of infected individuals as both spherical and filamentous particles, and proportions of the L, M and S polypeptides in these three forms varies appreciably.

The immunologic markers of HBV infection include the surface antigen (HBsAg), the core antigen (HBcAg), the "e" antigen (HBeAg) and their respective antibodies as well as virus polymerase and x antigen ("HBxAg"). Antibodies against HBsAg are protective against HBV infection.

The hepatitis B virus nucleocapsid plays a central role in the production of infectious "Dane" particles. During the formation of the virus, the core particle must recruit into its structure the essential ingredients of viral replication, the pregenomic RNA and the viral reverse transcriptase. On its completion, the core particle must migrate to the endoplasmic reticulum, where the viral surface antigens and lipids are continuously assembled into envelope structures, and delivered to the extracellular environment via the secretory pathway. Thus, formation of the infectious virion requires the nucleocapsid to "capture" the assembling surface proteins and pass through the secretory passageway.

Antibodies to proteins have been generated by immunization with short peptides having an amino acid sequence corresponding to the sequence of preselected protein fragments. Nima, et al, PNAS USA, 80: 4949–4953 (1983). Nevertheless, the generation of antibodies which recognize the native protein may depend on the appropriate conformation of the synthetic peptide immunogen, among other factors. Neurath et al., PNAS, 79:7871–7875 (1982). For this reason, immunization with synthetic peptide analogues of various virus proteins has only rarely resulted in production of virus-neutralizing antisera comparable to those elicited by the virus proteins themselves. Thus the preparation of synthetic immunogens mimicking antigenic determinants on intact viruses remains a challenge.

It has been suggested that HBV cores are not released from the cell without expression of envelope proteins, in contrast to the situation observed in retroviral assembly in general, where nucleocapsids can be exported in the absence of envelope gycoproteins. Bruss et al., PNAS, 88 1062–1063 (1991).

Certain vaccines have been described containing peptides with an amino acid chain of at least six consecutive amino acids within the pre-S gene coded region of the envelope of the hepatitis B virus. U.S. Pat. No. 5,204,096. However, these peptides do not appear to inhibit the assembly of the virus.

No safe and effective therapeutic treatment is presently available for hepatitis B infection, and clinical exploration of promising antiviral agents, such as nucleoside analogues, is hampered because of significant side-effects, resulting, for example, from their a specific body distribution.

Thus, there is a need for effective therapeutic and/or prophylactic agents against infection and diseases associated with HBV. The need has become even more urgent in view of the recent emergence of escape mutants of HBV that are not neutralized by vaccine induced antibodies.

SUMMARY OF THE INVENTION

Accordingly, the present invention is directed to novel peptides, and methods of treatment of diseases associated with HBV, which substantially obviate one or more of the problems due to the limitations and disadvantages of the related art. The peptides and small molecules taught and described herein are useful specifically for inhibiting the assembly of the HBV, thereby preventing disease and spread of infection.

Additional features and advantages of the invention will be set forth in the description which follows, and in part will be apparent from the description, or may be learned by practice of the invention. The objectives and other advantages of the invention will be realized and attained by the compositions, and methods particularly pointed out in the written description and claims hereof, as well as the appended drawings.

To achieve these and other advantages, and in accordance with the purpose of the invention, as embodied and broadly described herein, the invention relates to isolated, purified peptides which inhibit the assembly of the hepatitis B virus by binding to the core antigen of the virus, and thus prevent binding of the core antigen to the surface antigen. Specifically, the invention is directed to peptides which have a half maximal concentration ($IC_{50}$) less than about 5, preferably less than 2, more preferably less than about 1, and most preferably less than about 0.5 $\mu$M. Preferred peptides include, but are not limited to SLLGRMKG($\beta$-A)C (SEQ ID NO: 30), RSLLGRMKGA (SEQ ID NO: 31), HRSLLGRMKGA (SEQ ID NO: 32), MHRSLLGRMKGA (SEQ ID NO: 33), and RSLLGRMKGA($\beta$-A)C (SEQ ID NO: 34), or peptides derived therefrom.

In other embodiments, the invention is directed to compositions for inhibiting the assembly of the hepatitis B virus comprising the peptides described above. Further embodiments encompass methods of treatment and prevention, as well as pharmaceutical compositions such as vaccines.

It is to be understood that both the foregoing general description and the following detailed description are exemplary and explanatory and are intended to provide further explanation of the invention as claimed.

DETAILED DESCRIPTION

Reference will now be made in detail to the presently preferred embodiments of the invention, examples of which are set forth in the accompanying drawings.

The present invention provides peptides and other small molecules which are useful in inhibiting the assembly of HBV virus. The invention also provides a means for identifying additional peptides or small molecules which, in combination or alone, are capable of inhibiting viral assembly. Furthermore, the invention provides peptides which may be useful in therapeutic and vaccinal compositions, as well as methods of making these compositions, and methods of treating infected individuals. In applicants previous work, peptide sequences that bind to the core antigen of hepatitis B virus (HBcAg) were identified by selection from a random phage display library and their affinities in solution determined in the phage associated form. The free peptide, ALLGRMKG (SEQ ID NO: 16), derived from the selected fusion phage sequences, was able to inhibit the interaction between the long hepatitis B virus surface antigen (L HBsAg) and HBcAg, with a half maximal concentration (IC50) of 10 $\mu$M.

In an attempt to find improved inhibitors, a series of variants of the peptide ALLGRMKG (SEQ ID NO: 16) were provided by Drs. S. Adams and H. Cuervo (Biogen Inc.). However, none of these variants was an improvement over the initial sequence.

The present invention describes an alternative approach to the identification of improved inhibitors of L HBsAg binding to HBcAg, and encompasses peptides having a half maximal concentration ($IC_{50}$) of less than about 5. Preferably, the peptides of the invention have an $IC_{50}$ of less than about 2, more preferably, less than about 1, and most preferably, less than about 0.5 $\mu$M.

As used herein, the term "peptides" refers to peptides, fragments, and analogs thereof, which, alone or in combination, are useful in inhibiting the assembly of the HBV virus. Preferably, the peptides are between about 2 to about 20 amino acids in length. More preferably, the peptides are between about 3 to about 12 amino acids in length. Such peptides can include the specific peptides identified in the tables below, as well as fragments and analogs thereof.

As used herein, the term "fragment" refers to an amino acid sequence which is shorter than the peptide inhibitor from which it is derived, but which retains biological activity substantially identical to the original peptide. Preferably, such a fragment is at least two amino acids in length.

As used herein, the term "analog" refers to variations in the amino acid sequences of the inhibitor peptides, which may typically include analogs that differ by only one to about four amino acid changes. Other examples of analogs include peptides with minor amino acid variations from the inhibitors disclosed herein. In particular, peptides containing conservative amino acid replacements, i.e., those that take place within a family of amino acids that are related in their side chains, constitute analogs of the invention.

Genetically encoded amino acids are generally divided into four families: (1) acidic: aspartate, glutamate; (2) basic: lysine, arginine, histidine; (3) nonpolar: alanine, valine, leucine, isoleucine, proline, phenylalanine, methionine, tryptophan; and (4) uncharged polar: glycine, asparagine, glutamine, cysteine, serine, threonine, tyrosine. Phenylalanine, tryptophan, and tyrosine are sometimes classified jointly as aromatic amino acids. In the present invention, for example, it is reasonable to expect that an isolated replacement of leucine with an isoleucine or valine, an aspartate with a glutamate, a threonine with a serine, or a similar conservative replacement of an amino acid with a structurally related amino acid will not have a significant effect on its activity.

As used herein, the term "homologous peptide" includes peptide fragments which share at least 60 percent identity at the amino acid level, and preferably 75 percent identity, and substantially similar biological activity to a reference peptide. These preferred percentages reflect the small size of the peptides.

Peptide fragments which are particularly suited to the present invention are illustrated in Table 1.

The peptides, fragments, and analogs thereof, optionally associated with fusion partners, are preferably synthesized using conventional synthesis techniques, e.g., by chemical synthesis techniques. Alternatively, a skilled artesan may synthesize any of the peptides of the present invention by using an automated peptide synthesizer using standard chemistry such as, for example, t-BOC chemistry. (See L. A. Carpino, J. Am. Chem. Society, 79: 4427 (1957), the disclosure of which is hereby incorporated by reference.)

Alternatively, the peptides and other constructs of the invention may be prepared by known genetic engineering techniques, e.g., recombinant DNA techniques by cloning and expressing within a host microorganism or cell a DNA fragment carrying a coding sequence for the selected peptide or construct. Coding sequences for the peptides, fragments and fusion proteins can be prepared synthetically, or can be derived from viral RNA by known techniques, or from available cDNA-containing plasmids.

For use in the compositions and methods of the invention, it is anticipated that the above-described peptides, fragments and analogs thereof, may be designed into conventionally known, or alternative constructs to enhance production of the peptide or to enhance binding to HBcAg and thereby inhibit HBV assembly. For example, the peptides may optionally be fused to a protein or peptide fusion partner. Thus, one of skill in the art may design the peptide in association with a selected fusion partner, such as another peptide of the invention, or other peptides or proteins which impart desirable characteristics to the inhibitor peptide. Similarly, it is possible for one skilled in the art to engineer a peptide of the present invention as a fusion with an antibody or a fragment thereof.

Systems for cloning and expressing the peptides of the invention in various microorganisms and cells, including, for example, *E-coli,* bacillus, streptomyces, saccharomyces, mammalian, yeast and insect cells, and suitable vectors therefore, are known and available from private and public laboratories and depositories and from commercial vendors.

Whether produced recombinantly or synthesized, the peptides of the invention may be purified using conventional purification means. One of skill in the art can readily determine the appropriate level of purity required for the desired application for which the peptides are to be used.

These peptides and fragments of the invention are also useful as diagnostic reagents and vaccine components useful in the treatment of hepatitis B infection. The peptides and molecules disclosed herein may also be associated with a diagnostic label, a chemical marker, a toxin, or another protein or peptide, provided that the peptide associated with such a molecule is characterized by substantially the same biological activity as the original peptide.

The present invention also provides a means for identifying additional peptides which may inhibit the assembly of the hepatitis B virus. According to this method, one skilled in the art may also use HBsAg preparations to identify additional peptides which have analogous biological activity to the peptides disclosed herein, in that they also would inhibit the interaction between HBcAg and HBsAg, thereby preventing virus formation. Using techniques which are known to those skilled in the art, it is anticipated that the disclosure herein would enable one skilled in the art to identify other suitable peptides.

The peptides of the invention may be useful as diagnostic free agents, as well as therapeutics. Specifically, the peptides may be associated with conventional labels which are capable, alone or in combination with other compositions or compounds, of providing a detectable signal which would indicate the presence of the hepatitis B virus in a sample. A variety of enzyme systems have been described in the art which will operate to reveal, for example, a colorimetric signal in an assay, e.g., glucose oxidase, peroxide, tetramethylbenzadine systems (tmb), horse radish peroxidase (hrp) systems and other similar enzyme systems. Other label systems that may be utilized in the methods of this invention are detectable by other means, e.g., colored latex microparticles, magnetic particles, fluorescent compounds, radioactive compounds or elements, or immunoelectrodes.

Detectable labels for attachment to the peptides or constructs useful in the diagnostic assays of this invention may be easily selected from among numerous compositions known and readily available to one skilled in the art of diagnostic assays. The diagnostic methods and peptides of the invention are not limited by the particular detectable label or label system employed.

It will be understood by those skilled in the art that any number of conventional assay formats, particularly immunoassay formats, may be designed to utilize the peptides or constructs of the invention for the detection of HBV infection. This invention is thus not limited by the selection of the particular assay format, and is believed to encompass assay formats which are known to one of skill in the art. For convenience, reagents for assays according to this invention may be provided in the form of kits. These kits can include microtiter plates to which the peptides or constructs have been preabsorbed, various diluents and buffers, labeled conjugates for the detection of specifically bound peptides, and other signal generating reagents, such as enzyme substrates, cofactors and chromogens. Other components of these kits can easily be determined by one of skill in the art.

The present invention also provides compositions useful for therapeutic treatment of individuals infected with HBV or for vaccinations for preventing HBV infection. Such compositions comprise a peptide of the invention, a fragment or analog thereof, and may additionally contain pharmaceutically acceptable carriers or diluents suitable for administration for the treatment of such infections. Such compositions include a pharmaceutical preparation for the treatment of hepatitis B in mammals, said preparation comprising a therapeutically effective amount of a peptide which binds to HBcAg and interferes with the association of HBcAg and HbsAg; and a pharmaceutically acceptable carrier. Suitable pharmaceutically acceptable carriers will facilitate administration of the peptides, however, are physiologically inert and/or, nonharmful. Numerous carriers are known in the art and may be chosen based upon the desired application. Exemplary carriers include, but are not limited to, sterile saline, lactose, sucrose, calcium phosphate, gelatin, dextrin, agar, peptin, peanut oil, olive oil, sesame oil, and water. Additionally, the carrier or diluent may include a time delay material, such as glycerol monosterate or glycerol disterate, alone, or in combination with a wax. In addition, known slow release polymer formulations including, for example, soluble glasses, can be used.

In certain embodiments, a vaccine composition may contain a "cocktail" of multiple reagents useful in the treatment, or prevention, of hepatitis B infection. For example, a cocktail may include other reagents such as interferons, nucleoside analogs and/or N-acetyl-cysteine.

Optionally, the vaccine composition may further contain adjuvants such as conventional alum based adjuvants, or muramyl dipeptides, preservatives, chemical stabilizers or other antigenic proteins. Typically, stabilizers, adjuvants and preservatives etc. are optimized to determine the best formulation for efficacy in the desired application. Suitable preservatives may include chlorylbutynol, potassium sorbate, sorbic acid, sulfur dioxide, propyl gallade, parabens, glycerine, and phenol.

Suitable amounts of these compositions can be determined based upon the level of response desired. In general, the vaccine compositions may contain between 1 ng to 1000 mg of peptide. Suitable dosages of the vaccine composition of the invention can be readily determined as well. Generally, a suitable dose is between 0.1 to 5 milliliters of the vaccine composition. The dosage can also be determined readily by one skilled in the art based on the usual factors such as the weight, age, sex and/or general health of the patient being treated.

The present invention also provides a prophylactic method of administering to a subject an effective amount of the claimed composition. For example, for prevention of HBV infection, the claimed compositions may be administered as a vaccine which may be administered with a frequency which is dependent upon the likelihood of exposure to the virus. Where desirable, boosters may be co-administered. The vaccine may be administered by any suitable route, such as, for example parenteral administration, particularly intramuscular or subcutaneous, as well as oral administration. Thus, the present invention provides pharmaceutical compositions useful in providing passive immunity against infection by HBV.

The peptides claimed herein can be used in the active therapy of HBV infected individuals to inhibit, decrease, or slow the proliferation of the virus within the body. Therapeutic compositions comprise the claimed peptides capable of disabling, inhibiting or preventing the assembly mechanism of the virus. Such therapeutic compositions may be formulated to contain carriers or diluents, and one or more of the peptides of the invention. Such carriers and diluents are discussed above in connection with certain other compositions, and are readily identifiable by one of skill in the art. Optionally, the composition may contain other therapeutic agents useful against hepatitis B infection.

The peptides of the invention can be produced by recombinant DNA techniques in a host cell transformed with a nucleic acid sequence coding for the peptide, or by chemical synthesis, or in certain limited situations, by chemical cleavage of a protein or other methods. When produced by recombinant techniques, host cells transformed with nucleic acids encoding the peptide are cultured in a medium suitable for the cells, and recombinant peptides are purified from the cell culture medium, host cells, or both, using techniques known in the art. The recombinant peptides of the invention are isolated such that the peptide is substantially free of cellular material or culture medium when produced by recombinant DNA techniques, or substantially free of chemical precursors or other chemicals when synthesized chemically, or obtained by chemical cleavage of a protein.

Preparation of vaccines which contain peptide sequences as active ingredients is well understood in the art. Typically, such vaccines are prepared as injectable vaccines, either as liquid solutions or suspension. Solid forms suitable for solution or suspension in liquid prior to injection may also be prepared. The preparation may in certain embodiments be emulsified or encapsulated in liposomes. The active ingredient can be mixed with any number of excipients which are pharmaceutically acceptable and compatible with the active ingredient or ingredients.

EXAMPLES

Example 1

A selected peptide LLGRMK (SEQ ID NO: 36), in the phage associate form, was fused at the N termini of gpIII so that the sequence of the fusion protein would start:

ADGALLGRMKGA... gpIII sequence (SEQ ID NO: 1)

Random mutagenesis was performed on DNA encoding the peptide LLGRMKG (SEQ ID NO: 17) fused within the gpIII coat protein of fd phage. Initially this was performed using the Kunkel method of mutagenesis (4) with a primer designed to randomize the flanking amino acids A and G. A phage library was prepared by propagating the initial phage mutants and panning this against HBcAg on nitrocellulose discs, as described. Dyson & Murray, PNAS 92: 2194–2198 (1995). After three rounds of panning, binding phage were isolated, sequenced and purified for dissociation constant measurements. Dyson et al., Nucl. Acids Res. 23: 1531–1535 (1995). The most effective binder to HBcAg was one in which the N-terminal flanking alanine had been mutated to serine (phage 3). This exhibited a relative dissociation constant ($K_D^{Rel}$) of 1.7 nM and was a considerable improvement in binding affinity over the original "wild-type" sequence (phage B 1), with a $K_D^{Rel}$ of 152 nM (Table II). This improvement is caused by the addition of a hydroxyl group and one can postulate that this may be involved in hydrogen bonding with HBcAg.

A second generation of random mutation was performed by Kunkel mutagenesis on DNA encoding the peptide ADGSLLGRMKGA (SEQ ID NO: 6) fused to gpIII. A primer designed to randomize the G located adjacent the N-terminus and the C-terminal A was employed to construct a second phage display library which was panned against HBcAg. This was performed as described previously except that the panning took place at room temperature in polystyrene wells. The phage with the highest affinity in this case was phage 2A-8 where the glycine adjacent the N-terminus had been mutated to arginine. This displayed a $K_D^{Rel}$ of 1.1 nM (Table II). Primers were also employed to insert random 9-mer nucleotides between the codons for the G and S residues adjacent to the N terminus and the codons for G and A at the C terminus. Panning experiments using phage libraries derived from these primers resulted in a phage with enhanced affinity which had the tripeptide MHR inserted adjacent to the N terminus (phage 4A-15), with a $K_D^{Rel}$ of 0.55 nM (Table II).

Free peptides have been synthesized based on these phage with improved affinities (S. Adams and H. Cuervo), and these have been assayed for their ability to inhibit L HBsAg binding to HBcAg as shown in Tables 1 and 2. The best inhibitor thus far is the 10-mer peptide RSLLGRMKGA (SEQ ID NO: 31) which displays a $IC_{50}$ below 1 $\mu$M, representing greater than a 40 fold improvement over the original ALLGRMKG (SEQ ID NO: 16) peptide. Peptide AcSLLGRMKG (SEQ ID NO: 29) was synthesized to aid in hepatoma cell membrane transport. This peptide has been used by H. Takahashi and co-workers (Harvard Medical School) to test for the inhibition of HBV assembly in cultures of transfected hepatoma cells. Peptide SLLGRMKG($\beta$-A)C (SEQ ID NO: 30) was made for gold labeling in order to visualize the peptide binding to the surface of HBcAg capsids by cryo-electron microscopy in a collaboration with Dr. R. A. Cowther (University of Cambridge, England).

Example 2

Peptide ligands that bind to the core antigen (HBcAg) of HBV have been selected from a random hexapeptide library displayed on filamentous phage (Dyson & Murray, *Proc. Natl. Acad. Sci.* USA 92:2194–2198, 1995). These peptides inhibit the interaction between HBcAg and the viral surface antigen (HBsAg) in vitro. In this study, we investigated the inhibition of HBV production in transfected hepatoma cells by peptides containing the sequence LLGRMK (SEQ ID NO: 36) carried by one of the fusion phage. Methods: Hep G2 hepatoblastoma cells were transfected with a replication-competent HBV DNA construct (pHBV). The cells were transiently permeabilized with Trans-Port reagent (GIBCO BRL), and treated simultaneously with pHBV DNA and a synthetic peptide. (The extent of permeabilization was monitored by trypan blue staining.) Hep G2 cells were also transfected by the calcium phosphate method and treated with the peptides with or without permeabilization. To detect HBV production in transfected cells, HBV particles in test samples of the culture fluid were immunoprecipitated with monoclonal antibody specific for HBsAg, and then HBV DNA was analyzed by means of the polymerase chain reaction. Results: HBV production was substantially inhibited in transfected Hep G2 cells by peptides derived from the sequence LLGRMK (SEQ ID NO: 36) when these cells were transiently permeabilized during the treatment. This effect was not observed by control polypeptides that are incapable of blocking the interaction between HBcAg and HBsAg. Conclusions: These findings support the proposal that small peptide-based reagents may be effective for antiviral activity, or provide useful leads for such agents.

Inhibitors of the Association of HBsAg with HBcAg. The assay system developed for inhibitors of the interaction between HBsAg and HBcAg involved incubating purified membrane-inserted $^{35}S$-labeled L polypeptide in HBcAg-coated wells and quantitating bound protein by scintillation counting. The specificity of this interaction was established through its inhibition by various antibodies. Anti-HBcAg polyclonal serum inhibited the association of L HBsAg with HBcAg at a two-logarithmic higher dilution than preimmunized polyclonal serum from the same rabbit. Polyclonal serum raised against denatured S HBsAg inhibited the association reaction at a 1.5-logarithm-higher dilution than polyclonal serum against the native S HBsAg. The principal target for polyclonal antibodies to the native, particulate S HBsAg resides between as 110 and aa 150 (31–33). That antisera against denatured S HBsAg effectively inhibited the interaction between HBcAg and L HBsAg, whereas antibodies to native (S) HBsAg do not, probably reflects the presence of antibodies specific for cytoplasmically disposed epitopes of the membrane-bound S HBsAg that are normally hidden in the active form. Interestingly, the most effective inhibitor of the interaction between the two antigens was a monoclonal antibody (18/7) specific for a region close to the amino terminus of the pre-S1 domain, as 20–23 (4, 34), not previously thought necessary for virus formation (35). However, large molecules, such as immunoglobulins, can cause stearic hindrance over a considerable distance in any compound to which they bind.

The synthetic peptide ALLGRMKG (SEQ ID NO: 16), identified as a ligand to HBcAg via the fusion phage library, inhibited the reaction between the L HBsAg and HBcAg with 50% inhibition observed at a peptide concentration of 10 $\mu$M. The peptides GRMKG (SEQ ID NO: 19) and ALLTRILG (SEQ ID NO: 37) (the latter including as 21–27 of the S region) exhibited no inhibitory properties, in accord with their inability to inhibit binding of fusion phage to HBcAg. However, LDPAFR (SEQ ID NO: 38), which includes the epitope (residues 20–23) recognized by a monoclonal antibody (18/7) to the pre-S1 domain, did inhibit, but with a half-maximal effect at~360 $\mu$M.

The results provide evidence that sequences selected from the fusion phage library for binding to HBcAg do, indeed, mimic cytoplasmic regions of L HBsAg. Taken together with the observation of inhibition by monoclonal antibody 18/7, or a peptide containing its epitope, these results show that at least part of the contact region for HBcAg lies within the pre-S1 domain. The inhibition may be direct, with the peptides binding residues of HBcAg normally involved in HBsAg binding, or the peptides may bind to an alternative site and alter the conformation of the L HBsAg normally involved in HBcAg binding, or the peptides may bind to an alternative site and alter the conformation of the L HBcAg-binding domain in an allosteric manner. It should now be possible to map the binding site of the selected peptide on HBcAg, by chemical cross-linking, to identify specific amino acids of HBcAg that may be involved in recognition of the L HBsAg. An equivalent series of experiments with L HBsAg preparations may identify a corresponding mimotope of the binding domains of HBcAg. This approach should be generally applicable, not only to viral assembly, but to other complex biological assemblies such as ribosomes, spliceosomes, nucleosomes, proteasomes, and transcription complexes.

In addition to contributing to our understanding of HBV morphogenesis, the selected peptide ALLGRMKG (SEQ ID NO: 16) may represent a lead antiviral agent targeted at the inhibition of viral assembly; we are attempting to evaluate this in transformed hepatoma cells that produce the virus. Such compounds could be useful in chronic infections. The search for effective therapeutic agents against diseases associated with HBV has become more urgent with the recent emergence of escape mutants of HBV that are not neutralized by vaccine-induced antibodies. These approaches are encouraged by the recent demonstration that peptides taken from viral components can inhibit influenza, sindbis, and vesicular stomatitis virus formation Example 3

Materials. The hexapeptide fusion phage library (1) and *E. coli* strain K91Kan were from G. Smith (University of Missouri, Columbia). Monoclonal antibody 18/7 (purified IgG) was from K. H. Heermann and W. H. Gerlich (University of Göttingen, Göttingen, F.R.G.). Peptides ALLGRMKG (SEQ ID NO: 16), ALLTRILG (SEQ ID NO: 37), GRMKG (SEQ ID NO: 19), and LDPAFR (SEQ ID NO: 38) were obtained from the Chemistry Department at the University of Edinburgh.

Plasmids pMDHBs3 and pMDHBs4, encoding the L and S forms of HBsAg, respectively, were used as templates for in vitro transcription reactions. Both contained a T7 RNA polymerase promoter followed by a 586-by copy of the encephalomyocarditis virus RNA 5' noncoding region (ref. 16; Novagen), 5' to the HBsAg coding regions that were generated as EcoRI-Sal I DNA fragments from plasmid pHBV130 (17). PCR amplification was used to create EcoRi targets by double mutations at either $A^{922}\rightarrow G$ and $T^{923}\rightarrow A$ or $G^{1415}\rightarrow A$ and $G^{1419}\rightarrow C$ for the L- and S-coding fragments, respectively, and a downstream site for Sal I ($A^{2274}\rightarrow G$) common to both fragments.

Purification of Particles Comprising Full-Length or Truncated HBcAg. HBcAg was purified from *E. coli* RB 791 harboring various plasmids (Murray, K., et al., EMBO J. 3: 645–650 (1984)), except that the cell extract was precipitated by ammonium sulfate (35% saturation), dialyzed against TBS (50 mM Tris-HCl, pH 7.5/150 mM NaCl), applied to 8–40% sucrose gradients (12 ml; TBS), and centrifuged at 100,000×g (TH641 rotor, Sorvall) for 5 hr at 4° C. Fractions containing HBcAg were pooled, and proteins were judged to be >90% pure by densitometry on SDS/PAGE, analytical sucrose-gradient centrifugation, and immune reactivity. Denaturation of truncated HBcAg was achieved by heating a sample (1 mg/ml) to 85° C. for 5 min, clarification by centrifugation, and remeasuring the soluble protein concentration.

Isolation of Phage that Bind to HBcAg. Nitrocellulose membrane (BioBlot-NC, 0.45-$\mu$M pore size, Costar) was soaked in 15% (vol/vol) methanol/25 mM Tris base/250 mM glycine for 15 min and placed on a dot-blot apparatus; HBcAg [20 $\mu$l; 0.25 mg/ml in phosphate-buffered saline (PBS)] was then washed through the membrane. The excised circles were placed in siliconized microcentrifuge tubes containing blocking buffer [400 $\mu$l; bovine serum albumin (BSA) at 10 mg/ml/0.5% Tween/0.02% $NaN_3$/TBS] and left at 6° C. overnight. An aliquot of the phage library [$5\times10^{10}$ plaque-forming units (pfu)] was incubated with TBS (400 $\mu$l)/BSA (0.1 mg/ml)/Tween (0.5%) for 1 hr at 6° C., to absorb those phage that bind BSA. The discs were then placed in the same buffer containing the phage library and rotated at 6° C. for 4 hr and washed six times with wash buffer A (0.5% Tween/TBS) or wash buffer B (0.5% Tween/ 50 mM Tris-HCl, pH 7.5/0.5 M NaCl), with a 10-min interval between each wash. Finally, elution buffer (400 μl; 0.1 M HCl, titrated to pH 2.2 by the addition of solid glycine/BSA at 1 mg/ml) was added, and after 10 min eluates were neutralized by addition of Tris-HCl (38 μl, 1 M, pH 9), titered, and amplified. Amplified eluates were subjected to two further rounds of affinity enrichment. DNA was isolated from individual phage clones, and the nucleotide sequence was determined (22) by using primer 5'-AGTTTTGTCGTCTTTCC-3'. Selected phage plaques were amplified in 500-ml cultures and purified by PEG precipitation and equilibrium centrifugation in 31% (wt/wt) CsCl/TBS.

Phage-Binding Assay in Solution. HBcAg at various concentrations (0.3–10 μM) was incubated at 6° for 18 hr with fusion phage B1 ($10^9$ pfu/ml) in TBS/BSA (0.2 mg/ml)/ $NaN_3$ (0.02%). Aliquots (100 μl) of each mixture were transferred to polystyrene wells (no. 2585, Costar) that had been coated with HBcAg (20 μg/ml in PBS; 125 μl per well). After 1 hr at 6° C. the wells were washed 10 times with TBS/BSA at 0.2 mg/ml. Bound phage were recovered and titered as described in the previous section. All assays were done in triplicate. The HBcAg concentration range was 1.58–50 μM for experiments with phage B2 and B3 and was 0.63–20 μM for experiments with phage B4. For peptide inhibition experiments, fusion phage ($10^9$ pfu/ml; 200 μl) were incubated with various concentrations of peptide (1 mM–10 nM) in HBcAg-coated wells for 90 min at 6° C.

In Vitro Transcription, Translation, and Translocation. Templates for transcription were linearized by digestion with Sal I. Transcription reactions were done as described (23) by using T7 RNA polymerase (Promega). Synthetic RNAs were stored at −70° C. in 4 μl aliquots. Translations were done at 30° C. for 2 hr by using micrococcal nuclease-treated rabbit reticulocyte lysates (Flexi rabbit reticulocyte lysate system, Promega). Reactions (18 μl) contained 2 μl of a 1:10 dilution of the transcription reaction, 10 μl of rabbit reticulocyte lysate, 20 μM of amino acid mixture minus methionine, 0.7 μl of [$^{35}$S] methionine (1 Ci/mol, Amersham; 1 Ci=37 GBq), 0.6 mM $Mg(OAc)_2$, 120 mM KCl, and 2 mM dithiothreitol. Reactions were done in the presence or absence of 0.1 μg of HBcAg and 1.3 μl of canine pancreatic microsomal membranes (2 equivalents/μl; Promega).

Immunoprecipitations. Translation mixture (5 μl) was diluted to 200 μl with NET-gel buffer (50 mM Tris-HCl, pH 7.5/150 mM NaCl/0.1% Nonidet P-40/1 mM EDTA/0.25% gelatin/0.02% $NaN_3$), containing 2 mM dithiothreitol. Either undiluted anti-HBsAg (a 1:1 mixture of anti-native and anti-denatured HB sAg sera) or a 1:10 dilution of anti-HBcAg rabbit polyclonal serum (1.5 μl) was added to the mixture. Immunoprecipitation with protein A-Sepharose and analysis by SDS/PAGE were as described (24).

Inhibition of Membrane-Inserted L-Protein Binding to HBcAg by Antibodies and Peptides. Canine pancreatic microsomal membranes containing labeled protein were purified by layering the translation mixture (60 μl) on a 4-ml step gradient of 1-ml intervals of 77% (wt/vol), 30%, 20%, and 10% sucrose containing 20 mM Hepes (adjusted to pH 7.5 with NaOH)/2 mM dithiothreitol for fractionation by centrifugation (50,000 rpm, 2 hr at 4° C.; Sorvall model TsT 60.4 rotor). SDS/PAGE located the membrane-bound L protein predominantly at the 77%/30% sucrose interface. Sucrose gradient-purified L protein (4 μl) was diluted with NET-gel buffer (100 μl) containing various dilutions of either antibody or peptide for inhibition assays. Mixtures were incubated in HBcAg-coated wells (as in the paragraph Isolation of Phage that Bind to HBcAg) for 2 ½ hr at 4° C. and washed five times with NET-gel buffer with 10-min intervals. Wells were placed in scintillation vials containing Ecoscint A (5 ml; National Diagnostics) for quantitation of radioactivity.

It will be apparent to those skilled in the art that various modifications and variations can be made in the peptides and methods of the invention without departing from the spirit or scope of the invention. Thus, it is intended that the present invention cover the modifications and variations of the invention, provided that they come within the scope of the appended claims and their equivalents.

TABLE I $K_D^{Rel}$ Summary for Variants of Phage B1

| Phage | Sequence | $K_D^{Rel}$ (nM) |
|---|---|---|
| B1 | ADGALLGRMKGA . . . (SEQ ID NO: 1) | 152 ± 5 |
| 2 | ADGALLGRMKPA . . . (SEQ ID NO: 2) | 767 ± 8 |
| 1 | ADGSLLGRMKPA . . . (SEQ ID NO: 3) | 322 ± 50 |
| 6 | ADGALLGRMKRA . . . (SEQ ID NO: 4) | 181 ± 12 |
| 4 | ADGTLLGRMKLA . . . (SEQ ID NO: 5) | 20 ± 2 |
| 3 | ADGSLLGRMKGA . . . (SEQ ID NO: 6) | 1.7 ± 0.3 |
| 2A-8 | ADRSLLGRMKGA . . . (SEQ ID NO: 7) | 1.09 ± 0.02 |
| 4A-1 | ADGSRSSLLGRMKGA . . . (SEQ ID NO: 8) | 1.96 ± 0.32 |
| 4B-3 | ADGAHSSLLGRMKGA . . . (SEQ ID NO: 9) | 1.72 ± 0.17 |
| 4B-7 | ADGHRSSLLGRMKGA . . . (SEQ ID NO: 10) | 1.40 ± 0.13 |
| 4A-2 | ADGPRSLLGRMKGA . . . (SEQ ID NO: 11) | 0.84 ± 0.07 |
| 4A-3 | ADGAHRSLLGRMKGA . . . (SEQ ID NO: 12) | 0.94 ± 0.12 |
| 4A-28 | ADGYQRSLLGRMKGA . . . (SEQ ID NO: 13) | 0.88 ± 0.08 |
| 4A-26 | ADGTQRSLLGRMKGA . . . (SEQ ID NO: 14) | 0.84 ± 0.06 |
| 4A-15 | ADGMHRSLLGRMKGA . . . (SEQ ID NO: 15) | 0.55 ± 0.03 |

TABLE II

Summary of peptides inhibiting the association of L HBsAg with HBcAg

| Peptide | $IC_{50}$ (μM)[1] |
|---|---|
| ALLGRMKG (SEQ ID NO: 16) | 11.0 ± 0.8 |
| LLGRMKG (SEQ ID NO: 17) | 46.2 ± 7.4 |
| LGRMKG (SEQ ID NO: 18) | 980 ± 157 |
| GRMKG (SEQ ID NO: 19) | no[2] |
| LLGRM (SEQ ID NO: 20) | no |
| CLLGRMKC (SEQ ID NO: 21) | 652 ± 74 |
| ALLPRMKG (SEQ ID NO: 22) | no |
| SLLGRMKG (SEQ ID NO: 23) | 6.4 ± 0.7 |
| SLLGRMK (SEQ ID NO: 24) | 40.7 ± 4.8 |
| SLLGRMKGA (SEQ ID NO: 25) | 2.4 ± 0.2 |
| GSLLGRMKGA (SEQ ID NO: 26) | 0.79 ± 0.23 |
| DGSLLGRMKGAA (SEQ ID NO: 27) | 3.0 ± 0.4 |
| ADGSLLGRMKGAAG, (SEQ ID NO: 28) | 4.5 ± 0.8 |
| AcSLLGRMKG (SEQ ID NO: 29) | 26.2 ± 5.0 |
| SLLGRMKG(β-A)C (SEQ ID NO: 30) | 1.8 ± 0.4 |
| RSLLGRMKGA (SEQ ID NO: 31) | 0.29 ± 0.02 |
| HRSLLGRMKGA (SEQ ID NO: 32) | 0.50 ± 0.04 |
| MHRSLLGRMKGA (SEQ ID NO: 33) | 0.80 ± 0.10 |
| RSLLGRMKGA(β-A)C (SEQ ID NO: 34) | 0.29 ± 0.03 |
| MHRSLLGRMKGAG(β-A)GC (SEQ ID NO: 35) | 3.80 ± 0.69 |

[1]Concentration of peptide required to inhibit the binding of L HBsAg to HBcAg at a half maximal level.
[2]No observable inhibition.

What is claimed is:

1. An isolated, purified peptide that inhibits hepatitis B virus assembly by binding to the core antigen of hepatitis B virus and preventing the association of the core antigen with the surface antigen of hepatitis B virus, wherein said peptide comprises the sequence LLGRMKG (SEQ ID NO: 17) and has an $IC_{50}$ below 3 $\mu$M.

2. The peptide according to claim 1, wherein said peptide has an $IC_{50}$ below 1 $\mu$M.

3. The peptide according to claim 2, wherein said peptide has an $IC_{50}$ below 0.5 $\mu$M.

4. An isolated, purified peptide that inhibits hepatitis B virus assembly by binding to the core antigen of hepatitis B virus and preventing the association of the core antigen with the surface antigen of hepatitis B virus, wherein said peptide comprises a sequence selected from the group consisting of: SLLGRMKGA (SEQ ID NO: 25), DGSLLGRMKGAA (SEQ ID NO: 27), SLLGRMKG($\beta$-A)C (SEQ ID NO: 30), RSLLGRMKGA (SEQ ID NO: 31), HRSLLGRMKGA (SEQ ID NO: 32), MHRSLLGRMKGA (SEQ ID NO: 33), and RSLLGRMKGA($\beta$-A)C (SEQ ID NO: 34) and has an $IC_{50}$ below 3 $\mu$M.

5. A peptide selected from the group consisting of: SLLGRMKGA (SEQ ID NO: 25), DGSLLGRMKGAA (SEQ ID NO: 27), SLLGRMKG($\beta$-A)C (SEQ ID NO: 30), RSLLGRMKGA (SEQ ID NO: 31), HRSLLGRMKGA (SEQ ID NO: 32), MHRSLLGRMKGA (SEQ ID NO: 33), and RSLLGRMKGA($\beta$-A)C (SEQ ID NO: 34).

6. A composition for inhibiting the assembly of a hepatitis B virus virion, said composition comprising:
a) a peptide that binds to the core antigen of hepatitis B virus and interferes with the association of the core antigen with the surface antigen of hepatitis B virus, wherein said peptide comprises the sequence LLGRMKG (SEQ ID NO: 17) and has an $IC_{50}$ below 3 $\mu$M, said peptide being present in said composition in an amount effective to interfere with said association; and
b) a pharmaceutically acceptable carrier.

7. The composition according to claim 6, wherein said peptide has an $IC_{50}$ below 1 $\mu$M.

8. The composition according to claim 7, wherein said peptide has an $IC_{50}$ below 0.5 $\mu$M.

9. A composition for inhibiting the assembly of a hepatitis B virus virion, said composition comprising:
a) a peptide that binds to the core antigen of hepatitis B virus and interferes with the association of the core antigen with the surface antigen of hepatitis B virus, wherein said peptide is selected from the group consisting of: SLLGRMKGA (SEQ ID NO: 25), DGSLLGRMKGAA (SEQ ID NO: 27), SLLGRMKG ($\beta$-A)C (SEQ ID NO: 30), RSLLGRMKGA (SEQ ID NO: 31), HRSLLGRMKGA (SEQ ID NO: 32), MHRSLLGRMKGA (SEQ ID NO: 33), and RSLLGRMKGA($\beta$-A)C (SEQ ID NO: 34) and has an $IC_{50}$ below 3 $\mu$M, said peptide being present in said composition in an amount effective to interfere with said association; and
b) a pharmaceutically acceptable carrier.

10. The composition according to claim 6 or 9, further comprising a therapeutically effective amount of a reagent selected from the group consisting of an interferon, a nucleoside analog and N-acetyl-cysteine.

11. The composition according to claim 6 or 9, wherein said peptide is emulsified or encapsulated in a liposome.

12. The composition according to claim 11, wherein said peptide has an $IC_{50}$ below 1 $\mu$M.

13. The composition according to claim 12, wherein said peptide has an $IC_{50}$ below 0.5 $\mu$M.

14. A method for treating a mammal infected with hepatitis B virus comprising the step of administering to said mammal a therapeutically effective amount of a peptide that binds to the core antigen of hepatitis B virus and interferes with the association of the core antigen with the surface antigen of hepatitis B virus, wherein said peptide comprises the sequence LLGRMKG (SEQ ID NO: 17) and has an $IC_{50}$ below 3 μM, and thereby prevents assembly of the virus.

15. The method according to claim 14, wherein said peptide has an $IC_{50}$ below 1 μM.

16. The method according to claim 15, wherein said peptide has an $IC_{50}$ below 0.5 μM.

17. A method for treating a mammal infected with hepatitis B virus comprising the step of administering to said mammal a therapeutically effective amount of a peptide that binds to the core antigen of hepatitis B virus and interferes with the association of the core antigen with the surface antigen of hepatitis B virus, wherein said peptide is selected from the group consisting of: SLLGRMKGA (SEQ ID NO: 25), DGSLLGRMKGAA (SEQ ID NO: 27), SLLGRMKG(β-A)C (SEQ ID NO: 30), RSLLGRMKGA (SEQ ID NO: 31), HRSLLGRMKGA (SEQ ID NO: 32), MHRSLLGRMKGA (SEQ ID NO: 33), and RSLLGRMKGA(β-A)C (SEQ ID NO: 34) and has an $IC_{50}$ below 3 μM.

18. A diagnostic kit for detecting in vitro hepatitis B virus in a sample, said kit comprising:

a) a peptide that binds to the core antigen of hepatitis B virus and interferes with the association of the core antigen with the surface antigen of hepatitis B virus, wherein said peptide comprises the sequence LLGRMKG (SEQ ID NO: 17) and has an $IC_{50}$ below 3 μM, and thereby prevents assembly of the virus; and b) one or more reagents for detecting the binding of said peptide to the core antigen of hepatitis B virus.

19. The diagnostic kit according to claim 18, wherein said peptide has an $IC_{50}$ below 1 μM.

20. The diagnostic kit according to claim 19, wherein said peptide has an $IC_{50}$ below 0.5 μM.

21. A diagnostic kit for detecting in vitro-hepatitis B virus in a sample, said kit comprising:

a) a peptide that binds to the core antigen of hepatitis B virus and interfere with the association of the core antigen with the surface antigen of hepatitis B virus, wherein said peptide is selected from the group consisting of: SLLGRMKGA (SEQ ID NO: 25), DGSLLGRMKGAA (SEQ ID NO: 27), SLLGRMKG(β-A)C (SEQ ID NO: 30), RSLLGRMKGA (SEQ ID NO: 31), HRSLLGRMKGA (SEQ ID NO: 32), MHRSLLGRMKGA (SEQ ID NO: 33), and RSLLGRMKGA(β-A)C (SEQ ID NO: 34) and has an $IC_{50}$ below 3 μM.

22. A method for detecting in vitro hepatitis B virus in a sample, said method comprising the steps of:

a) contacting said sample with a peptide that binds to the core antigen of hepatitis B virus and interferes with the association of the core antigen with the surface antigen of hepatitis B virus, wherein said peptide comprises the sequence LLGRMKG (SEQ ID NO: 17) and has an $IC_{50}$ below 3 μM, and thereby prevents assembly of the virus, under conditions that permit said peptide to bind to any core antigen of hepatitis B virus in said sample; and b) detecting the binding of said peptide to the core antigen of hepatitis B virus.

23. The method according to claim 22, wherein said peptide has an $IC_{50}$ below 1 μM.

24. The method according to claim 23, wherein said peptide has an $IC_{50}$ below 0.5 μM.

25. A method for detecting in vitro hepatitis B virus in a sample, said method comprising the steps of:

a) contacting said sample with a peptide that binds to the core antigen of hepatitis B virus and interferes with the association of the core antigen with the surface antigen of hepatitis B virus, wherein said peptide is selected from the group consisting of: SLLGRMKGA (SEQ ID NO: 25), DGSLLGRMKGAA (SEQ ID NO: 27), SLLGRMKG(β-A)C (SEQ ID NO: 30), RSLLGRMKGA (SEQ ID NO: 31), HRSLLGRMKGA (SEQ ID NO: 32), MHRSLLGRMKGA (SEQ ID NO: 33), and RSLLGRMKGA(β-A)C (SEQ ID NO: 34) and has an $IC_{50}$ below 3 μM.

* * * * *

UNITED STATES PATENT AND TRADEMARK OFFICE
CERTIFICATE OF CORRECTION

PATENT NO. : 6,544,520 B1  Page 1 of 1
DATED : April 8, 2003
INVENTOR(S) : Kenneth Murray et al.

It is certified that error appears in the above-identified patent and that said Letters Patent is hereby corrected as shown below:

Title page
Item [54], change "HEPATITIS B VIRUS INHIBITORS" to -- NOVEL HEPATITIS B VIRUS INHIBITORS --

Column 1,
Line 1, insert "NOVEL".

Column 9,
Line 30, change "as 20-23" to -- aa 20-23 --.
Line 40, change "as 21-27" to -- aa 21-27 --.

Column 11,
Line 52, change "HB sAg" to -- HBsAg --.

Column 27,
Line 40, change "in vitro-hepatitis" to -- in vitro hepatitis --.
Line 43, change "and interfere" to -- and interferes --.

Signed and Sealed this

Eighteenth Day of November, 2003

JAMES E. ROGAN
*Director of the United States Patent and Trademark Office*